United States Patent [19]
Laughlin et al.

[11] Patent Number: 6,117,118
[45] Date of Patent: Sep. 12, 2000

[54] PROCESS FOR BLEACHING CHEMICALLY TANNED SKIN AND DISCOLORED NAILS

[75] Inventors: Anne M. Laughlin; Thomas J. Laughlin, both of Grapevine, Tex.

[73] Assignee: Laughlin Products, Inc., Grapevine, Tex.

[21] Appl. No.: 09/009,373

[22] Filed: Jan. 20, 1998

[51] Int. Cl.$^7$ .............................. A61M 35/00; A61K 7/44
[52] U.S. Cl. .......................... 604/290; 424/401; 424/59; 424/62
[58] Field of Search ................ 424/59–65, 401; 604/289, 290

[56] References Cited

U.S. PATENT DOCUMENTS

| | | | |
|---|---|---|---|
| 3,060,097 | 10/1962 | Fellows . | |
| 3,856,934 | 12/1974 | Kligman | 424/62 |
| 4,453,941 | 6/1984 | Jacobs | 424/59 |
| 4,826,681 | 5/1989 | Jacquet et al. | 424/613 |
| 5,456,211 | 10/1995 | Stevenson | 119/157 |
| 5,512,278 | 4/1996 | Mundschenk | 424/78.06 |
| 5,545,399 | 8/1996 | Lee et al. | 424/59 |
| 5,603,923 | 2/1997 | Robinson et al. | 424/60 |
| 5,700,452 | 12/1997 | Deckner et al. | 424/59 |
| 5,773,014 | 6/1998 | Perrier et al. | 424/401 |
| 5,880,314 | 3/1999 | Shinomiya et al. | 568/729 |

*Primary Examiner*—Corrine McDermott
*Assistant Examiner*—David J. Cho
*Attorney, Agent, or Firm*—Michael A. O'Neil

[57] ABSTRACT

In a process for bleaching chemically tanned skin and discolored nails, a bleaching composition is applied to the skin or nails to be bleached or lightened. The applied composition may be left undisturbed or may be rubbed into the skin continuously. The treatment period is about 30 seconds to 10 minutes in the case of skin, and about 5 minutes to 30 minutes in the case of nails. Thereafter the applied composition is removed from the skin or nails by a combination of towel wiping and water rinsing. The bleaching composition may include a bleaching agent comprising hydrogen peroxide and may include an activator comprising ammonium bicarbonate. The bleaching composition may also include an exfoliant comprising fine abrasive particles such as ground walnut shells, pumice or sand.

3 Claims, No Drawings

PROCESS FOR BLEACHING CHEMICALLY TANNED SKIN AND DISCOLORED NAILS

TECHNICAL FIELD

The present invention relates generally to a process for bleaching chemically tanned skin and nails, and more particularly to a process for gradually lessening unwanted coloration of the skin resulting from the application of chemical tanning agents, and also the bleaching of nails discolored by fungal growth or other nail disorders.

BACKGROUND AND SUMMARY OF THE INVENTION

The deleterious effects of over-exposure to sunlight are well known. Many dermatologists now advise their patients to minimize exposure to the sun. Nonetheless, many individuals are willing to risk these adverse effects to obtain a suntan. The use of artificial lighting systems which emulate sunlight to effect tanning can lead to similar adverse side effects.

Increased awareness of the harmful effects of tanning by means of radiation, along with a continued desire by many to be tanned, has led to an increased interest in tanning by means of chemical agents. The chemicals which are currently used in chemically or cosmetically tanning human skin include:

A. Agents which react with skin to form a color complex, such as dihydroxyacetone;

B. Bronzing agents such as juglone and lawsome; and

C. Dyes, such as food colorants.

It is also known to use combinations of the foregoing tanning agents to achieve a desired tanning effect.

Until very recently, the only methods available to apply chemical tanning agents have been manual in nature. For example, many commercially available chemical tanning compositions are provided in the form of creams, lotions, and sprays. All known manual techniques for applying chemical tanning agents are unsatisfactory to a greater or lesser degree because they result in streaking and blotching of the skin due to the application of uneven quantities of chemical tanning agents to localized areas of the skin, oil do to areas of skin tanning to different degrees even though they were exposed to similar quantities of tanning agents. Undesired streaking or blotching is usually observed when chemical tanning agents are manually applied no matter how careful the manual application may be.

The co-pending application of Thomas J. Laughlin discloses a system for automatically coating the human body which is capable of applying chemical tanning agents to human skin much more uniformly than is possible utilizing manual application techniques. Notwithstanding the highly improved results from the use of the Laughlin system, uneven tanning results can still occur. For example, the skin may be exposed to perspiration, rain, water spray, etc., following the application of tanning agents. Mechanical contact with the skin prior to the completion of the tanning process can also lead to uneven tanning results.

Regardless of the cause, even a minor amount of unevenness in coloration resulting from the application of a chemical tanning agent is considered unsatisfactory. Therefore, a need exists for a process for bleaching chemically tanned skin which can be easily and conveniently used to lighten streaks, blotches and other excessively dark areas resulting from this tanning process. Preferably, the bleaching results obtained by the use of the process are gradual in nature so that the previously excessively dark areas are easily blended with the coloration of surrounding areas, or to the desired color intensity.

The aforementioned tanning chemicals can also color nails. The resulting coloration, which is typically brown, is usually considered cosmetically undesirable. Nails can also be discolored by fungal growth or other nail disorders. The resulting color is usually brown, and in some cases black. There is a need for a bleaching process to return the discolored nails back to their natural color.

The present invention comprises a process for bleaching chemically tanned skin which fulfills the foregoing and other requirements which are entirely lacking in the prior art. In accordance with the broader aspect of the invention, a bleaching agent applied to selected areas of the skin for between about 30 seconds and about ten minutes and is thereafter removed. In accordance with the preferred embodiment of the invention, each application of the bleaching agent results in a reduction of the coloration of the area of the skin to which it is applied by about one or more shades. This allows excessive coloration of certain areas of the skin to be gradually reduced until the color of such areas is matched to and blends with the color of surrounding areas, or to the desired color intensity. The bleaching process can be enhanced in the case of thickened or callous skin by the use of an exfoliating agent in combination with the bleach, along with continuous rubbing during the treatment period. This invention can also be used to bleach nails discolored by chemical tanning agents, by fungal growth, or by other nail disorders. The application time in the case of nails is from about 5 minutes to about 30 minutes, with multiple applications sometimes required. With the proper application, the discolored nail can be bleached back to its natural color.

DETAILED DESCRIPTION OF THE INVENTION

In accordance with the broader aspects of the invention, chemically tanned skin and discolored nails are bleached or lightened utilizing a bleaching composition that is applied directly onto the skin or nails. The bleaching composition may also include an activator, which may include ammonium bicarbonate.

In accordance with a second embodiment of the invention, the bleaching composition is mixed with an exfoliant prior to application to the skin or nails. The exfoliant preferably includes fine abrasive particles which enhance the bleaching or lightening process when applied and rubbed over the skin or nails during the treatment process. The fine abrasive particles may comprise ground walnut shells. Alternately, the fine abrasive particles may comprise pumice or sand.

In the practice of the processes comprising the first and second embodiments of the invention, the bleaching composition, including the exfoliant in the case of the second embodiment of the invention, is applied generously over the portion of the skin or nail to be bleached or lightened. The applied materials may be left undisturbed or may be continuously rubbed for the entire application time, with continuous rubbing preferred in the embodiment including the exfoliant. The preferred application time in the case of application to skin is about 30 seconds to about 10 minutes, and the preferred application time in the case of nails is from about 5 minutes to about 30 minutes, with multiple applications sometimes required. Bleaching or lightening of chemically tanned skin or discolored nails occurs during the treatment period, and is apparent after the bleaching agent is removed. The bleaching agent can be removed by mechanical means, such as rubbing with a towel, or by rinsing with water. The net result of the use of the present invention is the lightening of chemically tanned skin or discolored nails by one or more shades.

The formulations set forth in the following Examples have been found to be effective in bleaching or lightening chemically tanned skin and discolored nails:

Example 1

| | |
|---|---|
| Hydrogen peroxide (H$_2$O$_2$) | 3% |
| Water | 97% |

The above-described composition is a USP product, for example, Hydrogen Peroxide (U.S.P. 3%) available from Albertson's, Boise, Id. and was prepared for use as described in the product instructions.

The above-mentioned composition was applied sparingly to an area of stomach skin that had previously been tanned by the application of a chemical tanning agent thereto. The composition was left undisturbed for about 2 minutes. At the end of the treatment period, the composition was removed with a wet paper towel. The net result of the process was the lightening of the area of skin to which the composition was applied by about one shade.

Example 2

Cream base: Water
    Stearyl alcohol
    Hydrogen peroxide
    Mineral oil
    Laneth-16
    Ceteth-16
    Oleth-16
    Aloe extract
    Lanolin alcohol
    Steareth-16
    Phenacetin
    Phosphoric acid
Activator: Ammonium bicarbonate
    Silica The above-described composition is marketed as Sally Hansen Créme Bleach and Sally Hansen Créme Hair Bleach for Face by Del Laboratories, Inc., Farmingdale, N.Y. and was prepared for use as described in the product instructions.

The above-mentioned composition was applied generously to an area of stomach skin that had previously been tanned by the application of a chemical tanning agent thereto. The composition was left undisturbed for about 2 minutes. At the end of the treatment period, the composition was removed with a wet paper towel. The net result of the process was the lightening of the area of skin to which the composition was applied by about one shade.

The above-mentioned composition was applied generously to areas on the feet that had previously been tanned by the application of a chemical tanning agent thereto. The composition was left undisturbed for times varying from 30 seconds to 30 minutes. The applied materials were removed by rubbing with dry paper towels followed by an extensive water rinse. The net result of the process was the lightening of the area of the foot skin to which the composition was applied by about one or more shades, with the degree of lightening proportional to the length of the treatment period.

The above-mentioned composition was applied generously to the toenail of a large toe. The toenail had been previously exposed to chemical tanning agent, and was discolored to a light brown color. The composition was left undisturbed for 30 minutes. The applied composition was removed with a dry paper towel then rinsed with water. The net result of the process was the lightening to the toenail back to its original color.

Example 3

Cream base: Water
    Hydrogen peroxide
    Cetyl alcohol
    Stearyl alcohol
    Peg 20 stearate
    Phenacetin
    Stearic acid
    Mineral oil
    Methylparaben
    Propylparaben
Activator: Water
    Cetyl alcohol
    Petrolatum
    Emulsifying wax
    Ammonium hydroxide
    Mineral oil
    Sodium lauryl sulfate
    Methylparaben
    Propylparaben The above-captioned composition is marketed as Invisi-Bleach Bleaching Cream by Ardell Int'l, Inc., Los Angeles, Calif. and was prepared for use as described in the product instructions.

The above-described composition was applied generously to areas of skin that had previously been tanned by the application of a chemical tanning agent thereto. The composition was left undisturbed on the skin for treatment periods between about 30 seconds and about five minutes. At the end of the treatment period, the composition was removed by rinsing with water. The net result of the process was the lightening of the area of the skin to which the composition was applied by about one or more shades.

Example 4

Cream Bleach: Water
    Cetyl alcohol
    Glyceryl sterate
    Hydrogen peroxide
    Mineral oil
    Petrolatum
    Propylene glycol
    PEG-100 sterate
    Pentaerythrityl
    Tetracaprylate/caprate
    Dimethicone
    Fragrance
    Tocopheryl Acetate
    Phosphoric Acid
Accelerator Powder: Ammonium bicarbonate The above-described composition is marketed as Nair Cream Bleach by Carter Products, a division of Carter-Wallace, Inc., New York, N.Y. and was prepared for use as described in the product instructions.

The above-described composition was applied sparingly to an area of stomach skin that had been tanned two or more shades darker by the application of a chemical tanning agent thereto. The composition was left undisturbed on the skin for 3.5 minutes, then removed by extensive water rinsing. The net result of the process was the lightening of the area of skin back to its original color.

Example 5

Cream: Water
    Hydrogen peroxide
    Glyceryl stearate
    Isopropyl myristate
    Steraryl sterate
    Propylene glycol
    Stearic acid
    Stearamidopropyl dimethylamine
    Phosphoric acid
Accelerator: Ammonium Bicarbonate The above-described composition is marketed as Jolen Créme Bleach by Jolen, Inc., Fairfield, Conn. and was prepared for use as described in the product instructions.

The above-described composition was applied generously to areas of skin that had previously been tanned by the application of a chemical tanning agent thereto. The composition was left undisturbed on the skin for treatment periods between about 30 seconds and about five minutes. At the end of the treatment period, the composition was removed by rinsing with water. The net result of the process was the lightening of the area of the skin to which the composition was applied by about one or more shades.

Example 6

Bleaching Cream: Water
    Hydrogen peroxide
    Cetearyl alcohol
    Ceteareth-20
    Mineral oil
    Stearic acid
Activating Cream: Water
    Ammonium hydroxide
    Cetyl alcohol
    Sodium laurel sulfate
    Mineral oil
    Petrolatum
    D&C Red #33
    FD&C Red #4

The above-described composition is marketed as Nudit by Medtech Laboratories, Inc., Jackson, Wyo. and was prepared for use as described in the product instructions.

The above-described composition was applied generously to areas of skin that had previously been tanned by the application of a chemical tanning agent thereto. The composition was left undisturbed on the skin for treatment periods between about 30 seconds and about five minutes. At the end of the treatment period, the composition was removed by rinsing with water. The net result of the process was the lightening of the area of the skin to which the composition was applied by about one or more shades.

The above-described composition was also applied generously to areas of skin that had previously been tanned by the application of a chemical tanning agent thereto, but the applied material was rubbed continuously on the skin for treatment periods between about 30 seconds and about five minutes. At the end of the treatment period, the composition was removed by rinsing with water. The net result of the process was the lightening of the area of the skin to which the composition was applied by about one or more shades.

The above-described composition was applied generously to all 10 fingernails of a test subject. The fingernails had previously been discolored by the application of a chemical tanning agent thereto, The composition was left undisturbed on the nails for treatment periods between about 5 minutes to 10 minutes. At the end of the treatment period, the composition was removed by rubbing with a paper towel followed by rinsing with water. The net result of the process was the lightening of the fingernails to which the composition was applied by about one or more shades, returning them to their natural color.

The above-described composition was applied generously to all toenails of two subjects. The toenail had previously been discolored by the application of a chemical tanning agent thereto. The composition was left undisturbed on the toenails for treatment periods between about 20 minutes to 30 minutes. Multiple applications were required for the toenail on the big toe. At the end of the treatment period, the composition was removed by rubbing with a paper towel followed by rinsing with water. The net result of the process was the lightening of the toenails to which the composition was applied by about one or more shades. With use of multiple applications, it was possible to return the toenail to its natural color.

In some cases, the ability of the compositions described in the foregoing Examples to bleach the skin was enhanced by the use of skin exfoliating products. In particular, formulations containing fine abrasive particles were found to enhance the bleaching process of thick or callous skin when rubbed continuously over the treatment period. The formulations found effective when used in combination with the abovementioned compositions include:

Example 7

Deionized water
Sodium lauryl ether sulfate
Ground walnut shell
Ammonium lauryl sulfate
Cocamide DEA
Disodium laureth sulfosuccinate
DEA-styrene
Acrylates
Divinyl benzene copolymer
Ammonium nonoxynol-4 sulfate
Magnesium aluminum silicate
Sodium Chloride
PEG-6000 distearate
Cocoamidopropyl bentaine
DMDM hydantoin
Fragrance Apricot
Citric acid
Methylparaben
Propylparaben
Cetyl alcohol
Glyceryl stearate
Glycol sterate
Trisodium EDTA
Allantoin
dl-Pantherol
Sorbitol
Vitamin E Acetate
Retinyl palmitate (Vitamin A)
Vegetable color carotene The above-described composition is marketed as Nature Bath Walnut Shell Body Scrub by Nature Cosmetics, Inc., Rancho Cucamonga, Calif.

The above-identified composition was mixed with the composition identified above in Example 6. The mixing ratio was about six parts of material described in Example 6 and about four parts of the material described above in this example.

The above-described composition was applied generously to the entire area of skin of the two hands of a test subject, including callous skin, on several different occasions. In each case, the skin of the hands had been previously tanned by the application of a chemical tanning agent thereto. The composition was continuously rubbed into the skin for treatment periods of between 2 and 10 minutes. At the end of the treatment period, the applied materials were removed by wiping with a towel followed by water rinses. The net result of the process was the lightening of the hand skin by one or more shades, including the callous skin.

Example 8

Water
Pumice
Propylene glycol
Sodium laureth sulfate
Cocamidopropyl betaine
Polysorbate 80
Cetyl Acetate
Acetylated lanolin alcohol
Lauryl polyglucose
Magnesium aluminum silicate
Xanthan gum
Cocamide DEA
Sodium lauroyl sarcosinate
Fragrance
DMDM hydantoin
Citric acid
Tetrasodium EDTA
FD&C Yellow #05
FD&C Green #03

The above-described composition is marketed as Lava Liquid Hand Soap by Block Drug Company, Inc., Jersey City, N.J.

The above-identified composition was mixed with the composition identified above in Example 6. The mixing ratio was about equal parts of the two compositions.

The above-described composition was applied generously to the entire area of skin of the two hands of a test subject, including callous skin, on several different occasions. In each case, the skin of the hands had been previously tanned by the application of a chemical tanning agent thereto, The composition was continuously rubbed into the skin for treatment periods of between 2 and 10 minutes. At the end of the treatment period, the applied materials were removed by wiping with a towel followed by water rinses. The net result of the process was the lightening of the hand skin by one or more shades, including the callous skin.

Those skilled in the art will appreciate the fact that the compositions identified in the foregoing Examples are commercially available products. However, the use to which these products are put as described above is entirely new and novel. This is particularly true in the case of the compositions identified above for the bleaching of nails.

Although preferred embodiments of the invention have been described in the foregoing detailed description, it will be understood that the invention is not limited to the embodiments described, but it is capable of numerous rearrangements and modifications of parts and elements without departing from the spirit of the invention.

What is claimed is:

1. A process for bleaching chemically tanned skin including the steps of:

providing a bleaching composition designed for application to human skin and comprising about 3 percent hydrogen peroxide and about 97 percent water;

applying the bleaching composition to a predetermined area of skin previously colored by the application of a chemical tanning agent thereto;

allowing for a treatment period of about 30 seconds to about 10 minutes;

thereafter removing the bleaching composition from the skin by a combination of towel rubbing and water rinsing.

2. A process for bleaching chemically tanned skin including the steps of:

providing a chemical tan removal composition including a bleaching composition designed for application to human skin and an exfoliating agent selected from the group including finely ground walnut shells, pumice, and sand;

applying the chemical tan removal composition to a predetermined area of skin previously colored by the application of a chemical tanning agent thereto;

continuously rubbing the chemical tan removal composition into the chemically tanned skin for a time period of about30seconds and about 10 minutes;

thereafter removing the chemical tan removal composition from the skin by a combination of towel rubbing and water rinsing.

3. A process for bleaching discolored nails including the steps of:

providing a bleaching composition designed for application to fingernails and toenails and comprising about 3% hydrogen peroxide and about 97% water;

applying the bleaching composition to nails previously colored by the application of a chemical tanning agent thereto;

leaving the bleaching composition in contact with the nails for a treatment period of about 5 minutes to about 30 minutes;

thereafter removing the bleaching composition from the nails by a combination of towel rubbing and water rinsing.

* * * * *

UNITED STATES PATENT AND TRADEMARK OFFICE
CERTIFICATE OF CORRECTION

PATENT NO. : 6,117,118
DATED : September 12, 2000
INVENTOR(S): Thomas Laughlin

It is certified that error appears in the above-identified patent and that said Letters Patent are hereby corrected as shown below:

Col. 8, Claim 1, line 16, replace "percent water" with --percent inert ingredients including water--.
Col. 8, Claim 2, line 39, replace "about30seconds" with --between about 30 seconds--.
Col. 8, Claim 3, line 47, replace "97% water" with --97% inert ingredients including water--.

Signed and Sealed this

Seventeenth Day of April, 2001

*Attest:*

NICHOLAS P. GODICI

*Attesting Officer*   *Acting Director of the United States Patent and Trademark Office*